United States Patent
Sugawara et al.

[11] Patent Number: 5,945,108
[45] Date of Patent: Aug. 31, 1999

[54] WATER-AND OIL-REPELLENT POWDER FOR COSMETIC AND COSMETIC CONTAINING SAID POWDER

[75] Inventors: Yasuo Sugawara; Kazuo Shimamoto; Motonobu Kubo; Masamichi Morita; Tetsuya Masutani, all of Osaka, Japan

[73] Assignee: Daikin Industries Ltd., Osaka, Japan

[21] Appl. No.: 08/670,645

[22] Filed: Jun. 26, 1996

[30] Foreign Application Priority Data

Jun. 26, 1995 [JP] Japan ..................................... 7-159227

[51] Int. Cl.$^6$ ...................................................... A61K 7/48
[52] U.S. Cl. ........................ 424/401; 424/69; 424/78.02; 424/78.03; 526/243; 526/245
[58] Field of Search .......................... 424/69, 401, 78.02, 424/78.03; 526/243, 245

[56] References Cited

U.S. PATENT DOCUMENTS

| | | | |
|---|---|---|---|
| 3,959,462 | 5/1976 | Parks et al. ................................ | 424/70 |
| 4,792,444 | 12/1988 | Fukasawa et al. ......................... | 424/63 |
| 5,380,455 | 1/1995 | Tsuda et al. ........................ | 252/174.23 |

OTHER PUBLICATIONS

Gb 1049063, abstract, Nov. 23, 1966.
JP 58059–278 (Abstract), Apr. 8, 1983.
JP 62–250074 (Oct. 1987) Abstract.
JP 55–167209 (Dec. 1980) Abstract.

*Primary Examiner*—Jyothsna Venkat
*Attorney, Agent, or Firm*—Birch, Stewart, Kolasch & Birch, LLP

[57] ABSTRACT

Disclosed is water- and oil-repellent powder for cosmetic, containing a homopolymer of a polyfluoroalkyl group-containing (meth)acrylate (I) or a copolymer of the polyfluoroalkyl group-containing (meth)acrylate (I) and an alkyl (meth)acrylate (II) and/or a silicone macromonomer (III). A cosmetic containing water- and oil-repellent powder for cosmetic is superior in water- and oil-repellency and feel in use, and has almost no change of makeup.

5 Claims, No Drawings

WATER-AND OIL-REPELLENT POWDER FOR COSMETIC AND COSMETIC CONTAINING SAID POWDER

FIELD OF THE INVENTION

The present invention relates to water- and oil-repellent powder for producing a cosmetic which is superior in water- and oil-repellency, and feel in use, and has no deterioration of makeup, and a cosmetic containing said powder. Said water- and oil-repellent powder for a cosmetic is obtained by dissolving a polyfluoroalkyl group-containing (meth)acrylate homopolymer or a polyfluoroalkyl group-containing (meth)acrylate copolymer in an organic solvent.

BACKGROUND OF THE INVENTION

As a cosmetic containing powder, there are a foundation, face powder, a cheek color, an eye color, body powder, etc. Powder referred to as a loading pigment, a white pigment or a coloring pigment is usually formulated in these cosmetics. The loading pigment includes inorganic powder such as talc, kaolin, mica, etc., and organic powder such as protein powder, fish scale guanine, etc. The white pigment includes inorganic powder such as titanium oxide, zinc oxide, etc. The coloring pigment includes inorganic powder such as red oxide, black iron oxide, yellow iron oxide, etc., and organic powder such as lake, tar pigment, etc. The above powders are usually amphiphatic and have properties which are compatible with both water and oil. Therefore, a cosmetic prepared by formulating these powders is liable to get wet by water or a secretion such as sweat, sebum, etc., thereby causing a phenomenon of "change of makeup" wherein a color tone of the cosmetic per se is deteriorated or clarified to expose a color of the skin, or a cosmetic film is transferred and agglomerated by perspiration or a motion of the face.

As a technique of preventing the change of makeup caused by water or sweat, a method comprising surface-treating the powder with silicone to impart water-repellency to the powder has usually been used. However, this method could not prevent the change of makeup caused by sebum because the silicone has water-repellency and has no oil-repellency.

In order to prevent the change of makeup caused by sebum, a method comprising surface-treating the powder with a fluorine-containing compound to impart the water- and oil-repellency to the powder has been recently suggested.

For example, Japanese Patent Kokai Publication No. 250074/1987 (62-250074) discloses a method comprising using diethanolamine perfluoroalkylphosphate as a fluorine-containing compound, which has already been put to practical use. However, this fluorine-containing compound has a problem of the cost that it is very expensive. Another problem of the design is materials. The characteristics of the compound are not easily modified because of non-polymerizability. Also, there is a problem of production. The powder must be surface-treated in water because of its hydrophilic nature and, therefore, the production process becomes complicated.

Japanese Patent Kokai Publication No. 167209/1980 (55-167209) discloses a method comprising using a water- and oil-repellent of a polymer having a perfluoroalkyl group, but there was a problem that the water- and oil-repellency is not always imparted to the powder. Specifically, even if the powder is treated with a solution prepared by diluting a commercially available perfluoroalkyl group-containing acrylate polymer emulsion described in the Example of this Patent Publication with water, many parts of the emulsion are not absorbed on the powder surface and water- and oil-repellency can not be imparted.

SUMMARY OF THE INVENTION

A main object of the present invention is to provide water- and oil-repellent powder for cosmetic, affording a cosmetic which is inexpensive, can be produced in a simple production process, is superior in water- and oil-repellency and feel in use, and prevents makeup from coming off.

This object as well as other objects and advantages of the present invention will become apparent to those skilled in the art from the following description.

The present invention provides water- and oil-repellent powder for a cosmetic, containing a polymer having a repeating unit (A) derived from a polyfluoroalkyl group-containing (meth)acrylate represented by the general formula (I):

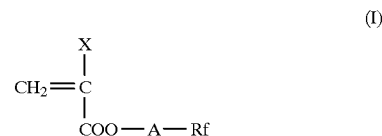

wherein Rf is a polyfluoroalkyl group having 6 to 16 carbon atoms; A is an alkylene group having 1 to 4 carbon atoms,

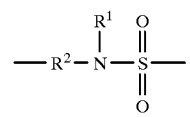

($R^1$ is an alkyl group having 1 to 4 carbon atoms, and $R^2$ is an alkylene group having 1 to 4 carbon atoms) or

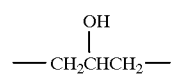

and X is a hydrogen atom or a methyl group.

The present invention also provides water- and oil-repellent powder for cosmetic, containing a copolymer having a repeating unit (B) derived from an alkyl (meth)acrylate represented by the general formula (II):

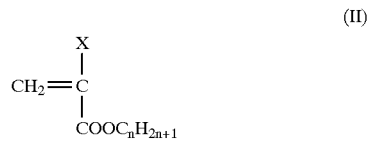

wherein X is a hydrogen atom or a methyl group; and n is 12 to 22, and/or a repeating unit (C) derived from a silicone macromonomer represented by the general formula (III):

$$CH_2 = \underset{\underset{COO-(CH_2)_3-\underset{\underset{CH_3}{|}}{Si}-O-(\underset{\underset{CH_3}{|}}{Si}-O)_m-\underset{\underset{CH_3}{|}}{Si}-CH_3}{|}}{\overset{\overset{CH_3}{|}}{C}} \quad (III)$$

wherein m is 5 to 200, in addition to a repeating unit (A) derived from a polyfluoroalkyl group-containing (meth)acrylate represented by the general formula (I):

$$CH_2 = \underset{\underset{COO-A-Rf}{|}}{\overset{\overset{X}{|}}{C}} \quad (I)$$

wherein Rf is a polyfluoroalkyl group having 6 to 16 carbon atoms; A is an alkylene group having 1 to 4 carbon atoms, $$-R^2-\underset{\underset{}{|}}{\overset{\overset{R^1}{|}}{N}}-\underset{\underset{O}{\|}}{\overset{\overset{O}{\|}}{S}}-$$

($R^1$ is an alkyl group having 1 to 4 carbon atoms, and $R^2$ is an alkylene group having 1 to 4 carbon atoms) or $$-CH_2\underset{\underset{}{}}{\overset{\overset{OH}{|}}{C}H}CH_2-$$

; and X is a hydrogen atom or a methyl group.

The present invention further provides a cosmetic comprising said water- and oil-repellent powder for cosmetic.

DETAILED DESCRIPTION OF THE INVENTION

In the present invention, combinations of monomers constituting the polymer are as follows:

(1) the polyfluoroalkyl group-containing (meth)acrylate (I) alone,
(2) the polyfluoroalkyl group-containing (meth)acrylate (I) and the alkyl (meth)acrylate (II),
(3) the polyfluoroalkyl group-containing (meth)acrylate (I) and the silicone macromonomer (III), and
(4) the polyfluoroalkyl group-containing (meth)acrylate (I), the alkyl (meth)acrylate (II) and the silicone macromonomer (III).

A polyfluoroalkyl group Rf in the polyfluoroalkyl group-containing (meth)acrylate (I) (hereinafter abbreviated to "FA") may be a perfluoroalkyl group. Examples of FA include the followings:
$CF_3(CF_2)_7(CH_2)OCOCH=CH_2$,
$CF_3(CF_2)_6(CH_2)OCOC(CH_3)=CH_2$,
$(CF_3)_2CF(CF_2)_6(CH_2)_2OCOCH=CH_2$,
$CF_3(CF_2)_7(CH_2)_2OCOC(CH_3)=CH_2$,
$CF_3(CF_2)_7(CH_2)_2OCOCH=CH_2$,
$CF_3(CF_2)_7SO_2N(CH_3)(CH_2)_2OCOCH=CH_2$,
$CF_3(CF_2)_7SO_2N(C_2H_5)(CH_2)_2OCOC(CH_3)=CH_2$, and
$(CF_3)_2CF(CF_2)_6CH_2CH(OH)CH_2OCOCH=CH_2$.

Two or more of FA may be used in combination.

The alkyl (meth)acrylate and the silicone macromonomer, which are fluorine-free monomers, are copolymerized with FA to obtain a FA copolymer.

Two or more of fluorine-free monomers may be used in combination.

In the FA copolymer, a weight ratio of FA to the fluorine-free monomer is from 6:4 to 9.9:0.1, preferably from 7:3 to 9:1. In the FA copolymer, the more a proportion of the fluorine-free monomer, the better the feel in use obtained by formulating it in the cosmetic (i.e. "removal" by the use of a puff and "spread" at the time of applying on the skin) becomes. When the weight ratio of FA to the fluorine-free monomer is larger than 6:4, the oil-repellency can not be imparted to the powder. A FA homopolymer is inferior to a copolymer in feel in use, but has a sufficient utility.

The FA homopolymer or FA copolymer used in the present invention is used in an amount of from 1 to 10 parts by weight, preferably from 3 to 7 parts by weight, based on 100 parts by weight of the powder. When the amount is smaller than 1 part by weight, the water- and oil-repellency can not be imparted. On the other hand, when the amount is larger than 10 parts by weight, the feel in use becomes inferior.

The FA homopolymer and FA copolymer used in the present invention can be produced by a bulk polymerization, a solution polymerization or an emulsion polymerization, using a polymerization initiator. Since the polymer is diluted with an organic solvent so as to surface-treat the powder with the FA homopolymer or FA copolymer, the polymer must be precipitated and dried in the case of the emulsion polymerization. In case of the bulk polymerization, there can be used a method comprising bubbling a nitrogen gas in FA alone or a mixture of FA and the fluorine-free monomer, introducing a polymerization initiator and polymerizing with stirring at a temperature within the range from 40 to 80° C. for several hours. In case of the solution polymerization, FA alone or the mixture of FA and the fluorine-free monomer is dissolved in an organic solvent in which these monomers are soluble, followed by polymerizing in a similar manner. In case of the emulsion polymerization, these monomers are emulsified in water, followed by polymerizing in a similar manner.

As the polymerization initiator, there can be used an oil-soluble polymerization initiator such as azobisisobutyronitrile, benzoyl peroxide, di-tertiary-butyl peroxide, lauryl peroxide, cumene hydroperoxide, t-butyl peroxypivalate, diisopropyl peroxydicarbonate, etc., and a water-soluble polymerization initiator such as benzoyl peroxide, lauroyl peroxide, tertiary-butyl perbenzoate, 1-hydroxycyclohexyl hydroperoxide, 3-carboxypropionyl peroxide, acetyl peroxide, azobisisobutylamidine dihydrochloride, sodium peroxide, potassium persulfate, ammonium persulfate, etc. The polymerization initiator is used in an amount of from 0.01 to 5 parts by weight, based on 100 parts by weight of the monomer. Upon the polymerization, a chain transfer agent and a pH adjustor may be optionally used. A molecular weight of the FA homopolymer or FA copolymer obtained after the polymerization is from 10,000 to 1,000,000, preferably from 20,000 to 300,000.

The organic solvent used for diluting the FA homopolymer or FA copolymer to surface-treat the powder contains a fluorine-containing solvent in an amount of not less than 60% by weight is used, preferably not less than 80% by weight. When in an organic solvent containing the fluorine-containing solvent in the amount of less than 60% by weight is used, no oil-repellency develops. The organic solvent used in the present invention may be a mixture of the fluorine-containing solvent and a fluorine-free solvent. Examples of the fluorine-containing solvent include a fluorinated hydrocarbon solvent such as HCFC-123, HCFC-141b, HCFC-225, CFC-113, CFC-316, etc., and a fluorocarbon solvent such as perfluorohexane, perfluorooctane, perfluorodecalin, perfluoromethyldecalin, perfluorotributylamine, perfluoropropylamine, etc. Examples of the fluorine-free solvent include a hydrocarbon such as n-hexane, n-heptane, toluene, benzene, etc., and a chlorine-containing solvent such as 1,1,2,2-tetrachloroethane, 1,1,1-trichloroethane, perchloroethylene, etc. Two or more of these organic solvents may be used in combination.

The FA homopolymer or FA copolymer is adhered to the surface of the powder by a wet method using an organic solvent. That is, a solution prepared by diluting the polymer as such or the polymer solution with the above organic solvent is mixed with the powder, and then the mixture is stirred at a room temperature or an elevated temperature until the powder gets wet uniformly with the organic solvent solution. At the stirring, a stirring device such as a Henschel mixer, a vibration ball mill, a rotary ball mill, a super mixer, a planetary mixer, etc. is used. When stirring in a laboratory scale, a domestic juicer mixer may be used. The concentration of the FA homopolymer or FA copolymer in the organic solvent solution is not specifically limited, but is adjusted so that the viscosity does not become large on the stirring when mixing the powder. After the stirring, the organic solvent is distilled off in vacuum or by heating, and then the treated powder is uniformly dispersed using the above stirring device. When stirring in the laboratory scale, a domestic juicer mixer or a speed cutter may be used.

In the present invention, an agent which is suitable for modifying the feel in use may be used in combination when it required on surface treatment. Examples of the agent for modifying the feel in use of the powder for cosmetic include lecithin, N-mono long-chain acyl basic amino acid, silicone, chitosan, collagen, wax, etc.

The powder treated with the FA homopolymer or FA copolymer in the present invention may be any one which is usually used for the cosmetic, and is not specifically limited. Examples of the powder include inorganic powder such as talc, kaolin, mica, mica-titanium, titanium oxide, iron oxide, magnesium oxide, zinc monooxide, zinc dioxide, heavy or light calcium carbonate, calcium secondary phosphate, aluminum hydroxide, barium sulfate, silica, alumina, silica gel, carbon black, antimony oxide, magnesium aluminosilicate, magnesium aluminometasilicate, synthetic mica, etc.; and organic powder such as protein powder, fish scale guanine, metal soap, polyvinyl chloride, nylon 12, fine crystal fibrous powder, tar colorant, lake, etc. When the powder is surface-treated with the FA homopolymer or FA copolymer, two or more of powders may be mixed. When the water- and oil-repellent powder is formulated in the cosmetic, two or more of water- and oil-repellent powders may also be mixed.

In the cosmetic of the present invention, the amount of the water- and oil-repellent powder may be from 1 to 100% by weight, preferably from 10 to 100% by weight based on all powder in the cosmetics. In the cosmetic, the untreated powder or silicone-treated powder may be used in combination. When the amount is smaller than 1% by weight, the water- and oil-repellency can not be imparted to the cosmetic. As the components other than the water- and oil-repellent powder in the cosmetic of the present invention, a suitable component selected from raw materials formulated in a usual cosmetic can be formulated according to the type of the objective cosmetic, in so far as the water- and oil-repellency of the powder is not adversely affected.

Examples of the raw material include solid or semisolid oils such as vaseline, lanolin, ceresin, microcrystalline wax, carnauba wax, candelilla wax, higher fatty acid, higher alcohol, etc.; flowing oils such as squarane, liquid paraffin, ester oil, diglyceride, triglyceride, silicone oil, etc.; fluorine-containing oils such as perfluoropolyether, perfluorodecalin, perfluorooctane, etc.; water- and oil-soluble monomers; surfactants; colorants such as inorganic and organic pigments, inorganic and organic pigments treated with silicone or fluorine-containing compound, and organic dyes; ethanol; preservatives; antioxidants; coloring matters; thickeners; pH adjustors; flavors; ultraviolet absorbers; humectants; blood circulation accelerators; cool-sensitive agent; antihidrotics; germicides; skin activators and the like.

The cosmetic of the present invention can be produced according to a usual method, and can be used for finish cosmetics such as a foundation, a face powder, a cheek color, an eye color, etc., and basic cosmetics such as a milky lotion, a cream, etc.

PREFERRED EMBODIMENTS OF THE INVENTION

The following Preparative Examples and Examples further illustrate the present invention in detail but are not to be construed to limit the scope thereof. The water- and oil-repellency of the water- and oil-repellent powders obtained in the following Examples and Comparative Examples was evaluated as follows.

Evaluation Method of Water- and Oil-Repellency of Water- and Oil-Repellent Powder Water- and oil-repellent powder was pressed (200 kgf/cm$^2$, one minute) using a tablet molding machine to obtain a tablet. Several drops of water (several $\mu$l) were dropped on the tablet and a contact angle was measured using a contact angle meter. The water-repellency was evaluated according to the following criteria.

Contact angle is maintained at 110 to 130°: ⊙

Water completely penetrates into the tablet immediately after adding dropwise: X Several drops of n-hexadecane (several $\mu$l) were dropped on the tablet and a contact angle was measured. The oil-repellency was evaluated according to the criteria in Table 1.

TABLE 1

| | |
|---|---|
| Contact angle is maintained at 80 to 100°: | ⊙⊙ |
| Contact angle is maintained at 50 to 79°: | ○ |
| Although contact angle is from 50 to 100° immediately after adding dropwise, n-hexadecane completely penetrates into the tablet after 10 minutes: | Δ |
| n-Hexadecane completely penetrates into the tablet immediately after adding dropwise: | X |

Evaluation Method of Duration of Makeup and Feel in Use of Powdery Foundation

A powdery foundation of Table 2 was prepared by using powder (water- and oil-repellent powder) obtained by treating a mixed powder (prepared by mixing titanium oxide, sericite, talc, yellow iron oxide, red oxide and black iron oxide in a weight ratio of 7:40:37.46:0.97:0.35:0.22) with a fluorine-containing compound.

TABLE 2

Formulation and production process of powdery foundation

| Component | Amount (% by weight) |
| --- | --- |
| Water- and oil-repellent powder | 40 |
| Silicone-treated sericite | 23 |
| Silicone-treated talc | 23 |
| Methylpolysiloxane (100 cs) | 12 |
| Diisostearyl malate | 1 |
| Glyceryl trioctanoate | 1 |

Production process: Powder components were mixed and pulverized using an atomizer and the mixture was transferred to a Henschel mixer. Then, an oil was added, followed by mixing uniformly. The resultant blend was charged in a mold and subjected to the press molding to give a powdery foundation.

On the other hand, according to the same manner as that described above except that a commercially available silicone-treated powder (mixture of silicone-treated titanium oxide, silicone-treated sericite, silicone-treated talc, silicone-treated yellow iron oxide, silicone-treated red oxide and silicone-treated black iron oxide in a weight ratio of 7:40:37.46:0.97:0.35:0.22) was substituted for the water- and oil-repellent powder in Table 2, a powdery foundation containing only silicon-treated powder was prepared.

The duration and feel in use of the powdery foundation were compared with those of a powdery foundation comprising only silicone-treated powder, and evaluated according to the following criteria. The evaluation was conducted by five professional panelists for sensory evaluation and the average was taken as the result.
Very good: ○○
Good: ○
Equivalent: Δ
Slightly bad: X
Very bad: XX

PREPARATIVE EXAMPLE 1

$CH_2=CHCOO(CH_2)_2(CF_2CF_2)_nCF_2CF_3$ (hereinafter referred to as "FA", a mixture of a compound wherein n is 3, a compound wherein n is 4 and a compound wherein n is 5 in a weight ratio of 5:3:1) (32 g), stearyl acrylate (StA, 8 g), perfluorohexane (79 g) and HCFC-141b (79 g) were charged in a four-necked flask equipped with a reflux condenser, a nitrogen introducing tube, a thermometer and a stirrer and, after heating to 50° C., the mixture was stirred in a nitrogen atmosphere for 30 minutes. Then, t-butyl peroxypivalate (trade name: PERBUTYL PV) (manufactured by Nippon Oils & Fats Co., Ltd.) (2 g) was added and the polymerization was conducted for 6 hours. A gas chromatography analysis of the resultant reaction solution revealed that at least 90% of monomers were polymerized. Ethanol was added to precipitate the resulting polymer which was dried in vacuum to give a FA/StA copolymer. A molecular weight of the resultant FA/StA copolymer was measured by GPC. As a result, a weight average molecular weight was 50,000 (in terms of polystyrene).

PREPARATIVE EXAMPLE 2

According to the same manner as that described in Preparative Example 1 except that a silicone macromonomer (trade name: SAIRAPLAIN FM-0721) (molecular weight: 5000) (manufactured by CHISSO CO., LTD) (8 g) was substituted for StA (8 g) of Preparative Example 1, a FA/silicone macromonomer copolymer (weight ratio of FA to FM-0721=8:2) was prepared. A weight average molecular weight of the copolymer was 40,000.

PREPARATIVE EXAMPLE 3

According to the same manner as that described in Preparative Example 1 except that StA (4 g) and SAIRAPLAIN FM-0721 (trade name) (4 g) were substituted for StA (8 g) of Preparative Example 1, a FA/StA/silicone macromonomer copolymer (weight ratio of FA:StA:FM-0721=8:1:1) was prepared. A weight average molecular weight of the copolymer was 45,000.

PREPARATIVE EXAMPLE 4

According to the same manner as that described in Preparative Example 1 except that FA (40 g) was substituted for FA (32 g) and StA (8 g) of Preparative Example 1, a FA homopolymer was prepared. A weight average molecular weight of the homopolymer was 60,000.

PREPARATIVE EXAMPLE 5

FA (48 g), StA (12 g) (weight ratio of FA to StA=8:2), deionized water (150 g), acetone (24 g), n-laurylmercaptan (0.06 g), stearyltrimethylammonium chloride (1.8 g) and polyoxyethyleneoctylphenyl ether (4.2 g) were mixed and, after heating to 60° C., the mixture was emulsified using a high-pressure homogenizer. The resultant emulsion was charged in a four-necked flask equipped with a reflux condenser, a nitrogen introducing tube, a thermometer and a stirrer. After maintaining at 60° C. in a nitrogen atmosphere for about one hour and stirring sufficiently, azobisisobutylamidine dihydrochloride (trade name: V-50) (manufactured by WAKO JUNYAKU CO., LTD) (0.3 g) was added and the polymerization was initiated. The mixture was stirred with heating at 60° C. for 3 hours to obtain a polymer emulsion. A gas chromatography analysis of the resultant emulsion revealed that at least 99% of monomers were polymerized. Ethanol was added to precipitate the resulting polymer which was dried with vacuum to give a FA/StA copolymer. A molecular weight of the resultant FA/StA copolymer was measured by GPC. As a result, a weight average molecular weight was 20,000.

COMPARATIVE PREPARATIVE EXAMPLE 1

According to the same manner as that described in Preparative Example 1 except that FA (20 g) and StA (20 g) were substituted for FA (32 g) and StA (8 g) of Preparative Example 1, a copolymer (weight ratio of FA to StA=5:5) was prepared. A weight average molecular weight of the copolymer was 45,000.

Example 1

A polymer solution prepared by dissolving the FA/StA copolymer (weight ratio of FA to StA=8:2) (2 g) of Preparative Example 1 in perfluorohexane (198 g) and a mixed powder (prepared by mixing titanium oxide, sericite, talc, yellow iron oxide, red oxide and black iron oxide in a weight ratio of 7:40:37.46:0.97:0.35:0.22) (40 g) were mixed for one minute using a juicer mixer. After perfluorohexane was distilled off by heating at 60° C. for several hours, the mixture was pulverized for 30 seconds in a speed cutter to obtain water- and oil-repellent powder. A powdery foundation was prepared by using the powder according to the formulation and production process of Table 2. The evaluation results are shown in Table 3.

Example 2

The same manner as that described in Example 1 was repeated, except that the FA/silicone macromonomer copolymer (weight ratio of FA to silicone macromonomer=8:2) (2 g) of Preparative Example 2 was substituted for the FA/StA copolymer (weight ratio of FA to StA=8:2) (2 g) of Preparative Example 1. The evaluation results are shown in Table 3.

Example 3

The same manner as that described in Example 1 was repeated, except that the FA/StA/silicone macromonomer copolymer (weight ratio of FA:StA:silicone macromonomer=8:1:1) (2 g) of Preparative Example 3 was substituted for the FA/StA copolymer (weight ratio of FA to StA=8:2) (2 g) of Preparative Example 1. The evaluation results are shown in Table 3.

Example 4

The same manner as that described in Example 1 was repeated, except that the FA homopolymer (2 g) of Preparative Example 4 was substituted for the FA/StA copolymer (weight ratio of FA to StA=8:2) (2 g) of Preparative Example 1. The evaluation results are shown in Table 3.

Example 5

The same manner as that described in Example 1 was repeated, except that the FA/StA copolymer (prepared by emulsion polymerization) (2 g) of Preparative Example 5 was substituted for the FA/StA copolymer (prepared by solution polymerization) (2 g) of Preparative Example 1. The evaluation results are shown in Table 3.

Comparative Example 1

The same manner as that described in Example 1 was repeated, except that the FA/StA copolymer (weight ratio of FA to StA=5:5) (2 g) of Comparative Preparative Example 1 was substituted for the FA/StA copolymer (weight ratio of FA to StA=8:2) (2 g) of Preparative Example 1. The evaluation results are shown in Table 3.

Comparative Example 2

A suspension prepared by diluting a commercially available water- and oil-repellent emulsion (solid content: 18%) (trade name: UNIDYNE TG-410) (manufactured by DAIKIN INDUSTRIES, LTD) (11.1 g) with water (189 g) and the mixed powder (40 g) which was the same as that used in Example 1 were mixed for one minute using a juicer mixer. The mixture was suction-filtered and then dried with heating at 60° C. for several hours. The resultant was pulverized for 30 seconds using a speed cutter to obtain water- and oil-repellent powder. The analysis of the fluorine content of this powder revealed that the water- and oil-repellent emulsion was scarcely absorbed on the powder. According to the same manner as that described in Example 1, a powdery foundation was prepared. The evaluation results are shown in Table 3.

Comparative Example 3

A suspension prepared by diluting a commercially available ethanolamine salt of perfluoroalkylphosphate (solid content: 15%) (trade name: UNIDYNE TG-101) (manufactured by DAIKIN INDUSTRIES, LTD) (13.3 g) with water (186 g) and the mixed powder (40 g) which was the same as that used in Example 1 were mixed for one minute using a juicer mixer. After the pH was adjusted to 3 or less by adding dilute hydrochloric acid, the mixture was suction-filtered. After drying with heating at 60° C. for several hours, the resultant was pulverized for 30 seconds using a speed cutter to obtain water- and oil-repellent powder. According to the same manner as that described in Example 1, a powdery foundation was prepared. The evaluation results are shown in Table 3.

TABLE 3

Evaluation results of water- and oil-repellent powder and powdery foundation

| | Fluorine-containing compound | Composition (weight ratio) | Polymerization method of polymer | Wet treating method | Water- and oil-repellent powder | | Powdery foundation | | |
|---|---|---|---|---|---|---|---|---|---|
| | | | | | Water-repellency | Oil-repellency | Duration of makeup | Spread | Removal (Coming off) |
| Example 1 | Preparative Example 1 | FA/StA = 8/2 | Solution polymerization | Solvent system | ○ | ○○ | ○○ | Δ | Δ |
| Example 2 | Preparative Example 2 | FA/Silicone macro monomer = 8/2 | Solution polymerization | Solvent system | ○ | ○○ | ○○ | Δ | Δ |
| Example 3 | Preparative Example 3 | FA/StA/Silicone macro monomer = 8/1/1 | Solution polymerization | Solvent system | ○ | ○○ | ○○ | Δ | Δ |
| Example 4 | Preparative Example 4 | FA alone | Solution polymerization | Solvent system | ○ | ○○ | ○○ | X | X |
| Example 5 | Preparative Example 5 | FA/StA = 8/2 | Emulsion polymerization | Solvent system | ○ | ○○ | ○○ | Δ | Δ |
| Comparative Example 1 | Comparative Preparative Example 1 | FA/StA = 5/5 | Solution polymerization | Solvent system | ○ | X | Δ | Δ | Δ |
| Comparative Example 2 | TG-410 | FA copolymer emulsion | | Aqueous system | X | X | X | X | X |
| Comparative Example 3 | TG-101 | Diethanolamine salt of perfluoroalkylphosphate | | Aqueous system | ○ | Δ | ○ | X | X |

What is claimed is:

1. A cosmetic comprising (1) a water- and oil-repellent powder, comprising
   a polymer having a repeating unit (A) derived from a polyfluoroalkyl group-containing (meth)acrylate represented by formula (I):

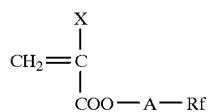
(I)

wherein Rf is a polyfluoroalkyl group having 6 to 16 carbon atoms; A is

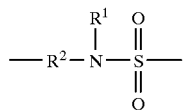

wherein $R^1$ is an alkyl group having 1 to 4 carbon atoms, and $R^2$ is

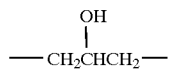

; and X is a hydrogen atom or a methyl group, and (2) an additive selected from the group consisting of oils, surfactants, colorants, ethanol, preservatives, antioxidants, coloring matters, thickeners, pH adjusters, flavors, ultraviolet absorbers, humectants and germicides.

2. A cosmetic comprising (1) a water- and oil-repellent powder, comprising a copolymer having a repeating unit (B) derived from an alkyl (meth)acrylate represented by formula (II):

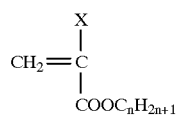
(II)

wherein X is a hydrogen atom or a methyl group; and n is 12 to 22, and a repeating unit (C) derived from a silicone macromonomer represented by formula (III):

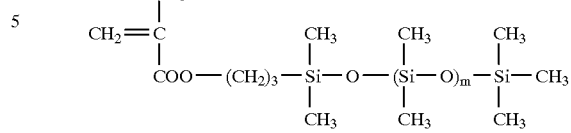
(III)

wherein m is 5 to 200, in addition to a repeating unit (A) derived from a polyfluoroalkyl group-containing (meth)acrylate represented by formula (I):

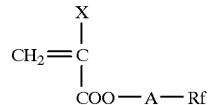

wherein Rf is a polyfluoroalkyl group having 6 to 16 carbon atoms; A is an alkylene group having 1 to 4 carbon atoms,

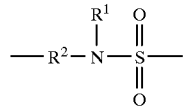

wherein $R^1$ is an alkyl group having 1 to 4 carbon atoms, and $R^2$ is

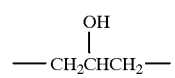

; and X is a hydrogen atom or a methyl group, and (2) a raw material selected from the group consisting of oils, surfactants, colorants, ethanol, preservatives, antioxidants, coloring matters, thickeners, pH adjusters, flavors, ultraviolet absorbers, humectants and germicides.

3. The A according to claim 2, wherein a weight ratio of the polyfluoroalkyl group-containing (meth)acrylate to the total of the alkyl (meth)acrylate and the silicone macromonomer in the copolymer is from 6:4 to 9.9:0.1.

4. The A according to claim 1 or 2, wherein the powder is obtained by dissolving the polymer in an organic solvent.

5. The A according to claim 4, wherein said organic solvent contains a fluorine-containing solvent in an amount of not smaller than 60% by weight.

* * * * *